United States Patent
Hallahan et al.

(10) Patent No.: US 6,486,170 B1
(45) Date of Patent: Nov. 26, 2002

(54) PHOSPHOLIPASE A2 INHIBITORS AS MEDIATORS OF GENE EXPRESSION

(75) Inventors: Dennis E. Hallahan, Des Plaines, IL (US); Ralph R. Weichselbaum, Chicago, IL (US); Donald W. Kufe, Wellesley, MA (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 08/248,058

(22) Filed: May 24, 1994

Related U.S. Application Data

(63) Continuation-in-part of application No. 08/192,107, filed on Feb. 4, 1994, now abandoned.

(51) Int. Cl.$^7$ ............................................... A61K 31/44
(52) U.S. Cl. ................. 514/297; 435/240.2; 435/173.1; 514/747; 514/263; 514/291; 514/297; 514/169
(58) Field of Search ........................... 435/173.1, 240.2; 514/747, 263, 291, 297, 169

(56) References Cited

U.S. PATENT DOCUMENTS

| | | | |
|---|---|---|---|
| 4,667,063 A | | 5/1987 | Mark et al. .................... 435/68 |
| 4,939,135 A | * | 7/1990 | Robertson .................... 514/179 |
| 5,354,756 A | * | 10/1994 | Underiner .................... 514/263 |

OTHER PUBLICATIONS

Nishida et al., Febs. Lett., 243(1), 25–9, 1989.*
Nishida et al., Ensho (Japanese Journal of Inflammation), 9(5), 397–402, 1989.*
Schandene et al., TransPlant Proc., 24(2, Suppl. 1), 55–61, 1993.*
Zabel et al., Int. Congr. Ser.—Excerpta. Med. 1020 (Bacteriol. Endotoxin), 413–21, 1993.*
Tsujimoto et al., Biochem. Biophys. Res. Comm., 153(1), 109–15, 1988.*
Chao e al., J. Infect. Dis., 166(4), 847–53, 1992.*
Edwards et al., J. Clin. Invest., 90(2), 637–41, 1992.*
Abou–Shoer et al., "Flavonoids From *Koelreuteria Henryi* And Other Sources As Protein–Tyrosine Kinase Inhibitors," *J. Nat. Proc.*, 56(6):967–9, 1993.
Al–Khodiary and Carr, DNA repair mutants defining $G_2$ checkpoint pathways in *Schizosaccharomyces pombe*, *The EMBO Journal*, 11(4):1343–1350, 1992.
Angel et al., "The jun Proto–Oncogene is Positively Autoregulated by its Product, Jun/AP–1," *Cell*, 55:875–885, 1988.
Atherton–Fessler et al., "Mechanisms of p34$^{cdc2}$ Regulation," *Molecular and Cellular Biology*, 13(3):1675–1685, 1993.
Barbet and Carr, "Fission yeast wee1 protein kinase is not required for DNA damage–dependent mitotic arrest," *Nature*, 364:824–827, 1993.

Baumann et al., "Response of Xenografts of Human Malignant Gliomas and Squamous Cell Carcinomas to Fractionated Irradiation," *J. Radiation Oncology Biol. Phys.*, 23(4):803–809, 1992.
Buchdunger et al., "4,5–Dianilinophthalimide: A protein–tyrosine kinase inhibitor with selectively for the epidermal growth factor receptor signal transduction pathway and potent in vivo antitumor activity," *Proc. natl. Acad. Sci. USA*, 91:2334–2338, 1994.
Budach et al., "The TCD$_{50}$ and Regrowth Delay Assay in Human Tumor Xenografts: Differences and Implications," *Int. J. Radiation Oncology Biol. Phys.*, 25, 259–268, 1993.
Carter et al., "Tyrosine phosphorylation of phospholipase C induced by membrane immunoglobulin in B lymphocytes," *Proc. Natl. Acad. Sci. USA*, 88:2745–2749, 1991.
Chan et al., "Selective inhibition of the growth of ras–transformed human bronchial epithelial cells by emodin, a protein–tyrosine kinase inhibitor," *Biochemical and Biophysical Research Communications*, 193(3):1152–1158, 1993.
Chen et al., "Structure of malhamensilipin A, an inhibitor of protein tyrosine kinase, from the cultured chrysophyte *poterioochromonas malhamensis*," *Journal of Natural Products*, 57(4):524–527, 1994.
De Boer et al., "Functional Evidence that the HECA–452 Antigen is Involved in the Adhesion of Human Neutrophils and Lymphocytes to Tumour Necrosis Factor–a–Stimulated Endothelial Cells," *Immunology*, 81:359–365, 1994.
Gillespie et al., "Inhibition of pancreatic cancer cell growth in vitro by the tyrphostin group of tyrosine kinase inhibitors," *Br. J. Cancer*, 68:1122–1126, 1993.
Hsu et al., "Inhibition Kinetics and Selectivity of the Tyrosine Kinase Inhibitor Erbstatin and a Pyridone–Based Analogue," *Biochemical Pharmacology*, 43(11):2471–2477, 1992.
Hwu et al., "Functional and Molecular Characterization of Tumor–Infiltrating Lymphocytes Transduced with Tumor Necrosis Factor–a cDNA for the Gene Therapy of Cancer in Humans," *The Journal of Immunology*, 150(9):4104–4115, May 1993.
Jayasuriya et al., Emodin, A Protein Tyrosine Kinase Inhibitor From *Polygonum Cuspidatum*, *J. Nat. Proc.*, 55(5):696–8, 1992).
Kakeya et al., "Isolation of a novel substrate–competitive tyrosine kinase inhibitor, desmal, from the plant *Desmos chinensis*," *FEBS*, 320(2):169–172, 1993.

(List continued on next page.)

Primary Examiner—Michael G. Wityshyn
(74) *Attorney, Agent, or Firm*—Fulbright & Jaworski

(57) ABSTRACT

A signaling pathway is identified that involves the activation of phospholipase A2 and protein kinase C in human cells, which in turn confers x-ray induction of the tumor necrosis factor α (TNF) gene. Inhibition of phospholipase A2 abolishes radiation-mediated arachidonate production, as well as the subsequent activation of protein kinase C and TNF gene expression. These phospholipase A2 inhibitors may be used to ameliorate the adverse-effects of radiotherapy associated with TNF production.

8 Claims, No Drawings

OTHER PUBLICATIONS

Khetarpal et al., "Dispositional characteristics of a tyrosine kinase inhibitor (RG 14620) in rats and rabbits following intravenous administration or dermal application," *Drug Metabolism and Disposition*, 22(2):216–223, 1994.

Larner et al., "Tyrosine Phosphorylation of DNA Binding Proteins by Multiple Cytokines," *Science*, 261:1730–1733, 1993.

Merkel et al., "Inhibition of EGF—Induced Vasoconstriction in Isolated Rabbit Aortic Rings with the Tyrosine Kinase Inhibitor RG50864," *Biochemical and Biophysical Research Communications*, 192(3):1319–1326, 1993.

Montefort et al., "Intercellular Adhesion Molecule–1 (ICAM–1) and Endothelial Leucocyte Adhesion Molecule–1 (ELAM–1) Expression int he Bronchial Mucosa of Normal and Asthmatic Subjects," *Eur. Respir. J.*, 5:815–823, 1992.

Nakamura et al., "Redox regulation of a src family protein tyrosine kinase p56$^{lck}$ in T cells," *Oncogene*, 8:3133–3139, 1993.

O'Connor et al., "Relationships between cdc2 Kinase, DNA Cross–linking, and Cell Cycle Perturbations Induced by Nitrogen Mustard," *Cell Growth & Differ.*, 3:43–52, 1992.

Ohmichi et al., "The Tyrosine Kinase Inhibitor Tyrphostin Blocks the Cellular Actions of Nerve Growth Factor," *Biochemistry*, 32:4650–4658, 1993.

Parker et al., "p107$^{wee1}$ is a dual–specificity kinase that phosphorylates p34$^{cdc2}$ on tyrosine 15," *Proc. Natl. Acad. Sci. USA*, 89:2917–2921, 1992.

Phillips et al., "ELAM–1 Mediates Cell Adhesion by Recognition of a Carbohydrate Ligand, Sialyl–Le$^x$," *Science*, 250:1130–1132, Nov. 1990.

Reid et al., "Resistance to Killing by Tumor Necrosis Factor in an Adipocyte Cell Line Caused by a Defect in Arachidonic Acid Biosynthesis," *J. Biol. Chem.*, 266(25):16580–16597, 1991.

Rewcastle et al., "Tyrosine Kinase Inhibitors. 3. Structure–Activity Relationships for Inhibition of Protein Tyrosine Kinases by Nuclear–Substituted Derivatives of 2,2'–Dithiobis (1–methyl–N–phenyl–1H–indole–3–carboxamide)," *J. Med. Chem.*, 37:2033–2042, 1994.

Spriggs et al., "Phospholipase A$_2$ Activation and Autoinduction of Tumor Necrosis Factor Gene Expression by Tumor Necrosis Faction," *Cancer Research*, 50:7101–7107, 1990.

Sugata et al., "Inhibition of Serum–Induced M–Phase Progression by a Tyrosine Kinase Inhibitor, Erbstatin," *Biochemical and Biophysical Communications*, 194(1):239–245, 1993.

Tanaka et al., "BE–23372M, A Novel Protein Tyrosine Kinase Inhibitor III. Synthesis," *Antibiot. (Tokyo)*, 47(3):297–300, 1994b.

Tanaka et al., "BE–23372M, A Novel Protein Tyrosine Kinase Inhibitor II. Physico–Chemical Properties and Structure Elucidation," *The Journal of Antibiotics*, 47(3):294–296, 1994.

Tartaglia and Goeddel, "Tumor Necrosis Factor Receptor Signaling," *J. Biol. Chem.*, 267(7):4304–4307, 1992.

Tartaglia and Goeddel, "Two TNF Receptors," *Immunology Today*, 13(5):151–153, 1992.

Tartaglia et al., "A Novel Domain Within the 55 kd TNF Receptor Signals Cell Death," *Cell*, 74:845–853, 1993.

Tartaglia et al., "Tumor Necrosis Factor's Cytotoxic Activity is Signaled by the p55 TNF Receptor," *Cell*, 73:213–216, 1993.

Teng et al., "Long–term Inhibition of Tumor Growth by Tumor Necrosis Factor in the Absence of Cachexia or T–cell Immunity," *Proc. Natl. Acad. Sci. USA*, 88:3535–3539, 1991.

Thakkar et al., "Synthesis and Protein–Tyrosine Kinase Inhibitory Activity of Polyhydroxylated Stilbene Analogues of Piceatannol," *J. Med. Chem.*, 36:2950–2955, 1993.

Veale et al., "Reduced Synovial Membrane Macrophage Numbers, ELAM–1 Expression, and Lining Layer Hyperplasia in Psoriatic Arthritis as Compared with Rheumatoid Arthritis," *Arthritis and Rheumatism*, 36(7):893–900, Jul. 1993.

Whelan et al., "An NF kB–Like Factor is Essential but not Sufficient for Cytokine Induction of Endothelial Leukocyte Adhesion Molecule 1 (ELAM–1) Gene Transcription," *Nucleic Acids Research*, 19(10):2645–2653, 1991.

Wong et al., "Antiviral Activity of Tumor Necrosis Factor (TNF) is Signaled Through the 55–dKa Receptor, Type I TNF," *J. of Immunology*, 149(10):3350–3353, 1992.

Yoneda et al., "The Antiproliferative Effects of Tyrosine Kinase Inhibitors Tyrphostins on a Human Squamous Cell Carcinoma in Vitro and in Nude Mice," *Cancer Research*, 51:4430–4435, 1991.

Brach et al., "Ionizing Radiation Induces Expression and Binding Activity of the Nuclear Factor $_k$B," *J. Clin. Invest.*, 88:691–695, 1991.

Cantley et al., "Oncogenes and Signal Transduction," *Cell*, 64:281–302, 1991.

Datta et al., "Involvement of Reactive Oxygen Intermediates in the Induction of c–jun Gene Transcription by Ionizing Radiation," *Biochemistry*, 31(35):8300–8306, 1992.

Enoch and Nurse, "Mutation of Fission Yeast Cell Cycle Control Genes Abolishes Dependence of Mitosis on DNA Replication," *Cell*, 60:665–673, 1990.

Gould et al., "Complementation of the Mitotic Activator, p80$^{cdc25}$, by a Human Protein–Tyrosine Phosphatase," *Science*, 250:1573–1576, 1990.

Hallahan et al., "Molecular Basis for the Use of Glucocorticoids, Nonsteroidals and Pentoxifylline to Minimize the Acute Effects of Radiotherapy," *Cancer Research*, 51:4565–4569, 1991.

Hallahan et al., "Increased tumor necrosis factor α mRNA after cellular exposure to ionizing radiation," *Proc. Natl. Acad. Sci. USA*, 86:10104–10107, 1989.

Hallahan et al., "Transcriptional regulation of the TNF gene by x–irradiation," *Proc. Am. Assoc. Cancer Res.*, 31(0):75, 1990.

Hallahan et al., "Protein kinase C mediates x–ray inducibility of nuclear signal transducers EGR1 and JUN," *Proc. Natl. Acad. Sci. USA*, 88:2156–2160, 1991.

Hallahan et al., "Tumor Necrosis Factor Gene Expression Is Mediated by Protein Kinase C following Activation by Ionizing Radiation," *Cancer Research*, 51:4565–4569, 1991.

Hallahan et al., "Ketoconazole Attenuates Radiation–Induction of Tumor Necrosis Factor," *Int. J. Radiation Oncology*, in press, 1994.

Hallahan et al., "Mechanisms of X–Ray Mediated Protooncogene c–jun Expression in Radiation–Induced Human Sarcoma Cell Lines," *Int. J. Radiation Oncology Biol. Phys.*, 21(6):1677–1681, 1991.

Hartwell and Weinert, "Checkpoints: Controls That Ensure the Order of Cell Cycle Events," *Science*, 246:629–634, 1989.

Hollander and Fornace, "Induction of fos RNA by DNA-damaging Agents," *Cancer Research*, 49:1687–1692, 1989.

Kastan et al., "Participation of p53 Protein in the Cellular Response to DNA Damage," *Cancer Research*, 51:6304–6311, 1991.

Lambert and Borek, "X-ray-Induced Changes in Gene Expression in Normal and Oncogene-Transformed Rat Cell Lines," *Journal of the National Cancer Institute*, 80(18):1492–1497, 1988.

Mustelin and Altman, "Dephosphorylation and activation of the T cell tyrosine kinase pp56$^{lck}$ by the leukocyte common antigen (CD45)," *Oncogene*, 5:809–813, 1990.

Neta et al., "Role of Interleukin 6 (IL–6) in Protection from Lethal Irradiation and in Endocrine Responses to IL–1 and Tumor Necrosis Factor," *The Journal of Experimental Medicine*, 175:689–694, 1992.

Nurse, "Universal control mechanism regulating onset of M–phase," *Nature*, 344:503–508, 1990.

Papathanasiou et al., "Identification of an x-ray-inducible human gene and its altered expression in ataxia telagiectasia," *Proceedings of the American Association for Cancer Research*, 31:304, 1990.

Pleiman et al., "Mapping of Sites on the Src Family Protein Tyrosine Kinases p55$^{blk}$, p59$^{fyn}$, and p56$^{lyn}$ Which Interact with the Effector Molecules Phospholipase C–γ, Microtubule–Associated Protein Kinase, GTPase–Activating Protein, and Phosphatidylinositol 3–Kinase," *Molecular and Cellular Biology*, 13(9):5877–5887, 1993.

Sherman et al., "Ionizing radiation regulates expression of the c–jun protooncogene," *Proc. Natl. Acad. Sci. USA*, 87:5663–5666, 1990.

Uckun et al., "Tyrosine phosphorylation is a mandatory proximal step in radiation–induced activation of the protein kinase C signaling pathway in human B–lymphocyte precursors," *Proc. Natl. Acad. Sci. USA*, 90:252–256, 1993.

Uckun et al., "Ionizing radiation stimulates unidentified tyrosine–specific protein kinases in human B–lymphocyte precursors, triggering apoptosis and clonogenic cell death," *Proc. Natl. Acad. Sci. USA*, 89:9005–9009, 1992.

Weichselbaum et al., "Radiation–resistant and repair–proficient human tumor cells may be associated with radiotherapy failure in head–and neck–cancer patients," *Proc. Natl. Acad. Sci. USA*, 83:2684–2688, 1986.

Weichselbaum et al., "X–Ray Sensitivity of Fifty–three Human Diploid Fibroblast Cell Strains from Patients with Characterized Genetic Disorders," *Cancer Research*, 40:902–925, 1980.

Yamanshi et al., "Activation of Src–like Protein–tyrosine kinase Lyn and its association with phosphatidylinositol 3–kinase upon C–cell antigen receptor–mediated signaling," *Proc. Natl. Acad. Sci. USA*, 89:1118–1122.

Hallahan et al., "Membrane–derived second messenger regulates x–ray–mediated tumor necrosis factor α gene induction," *Proc. Natl. Acad. Sci. USA*, 91:4897–4901, 1994.

Hallahan et al., "Inhibition of Protein Kinases Sensitizes Human Tumor Cells to Ionizing Radiation," *Radiation Research*, 129:345–350, 1992.

Herrlich et al., "DNA Damage–Induced Gene Expression: Signal transduction and Relation to Growth Factor Signaling," *Rev. Physiol. Biochem. Pharmacol.*, 119:187–223, 1992.

Nishizuka, "Intracellular Signaling by Hydrolysis of Phospholipids and Activation of Protein Kinase C," *Science*, 258:607–614, 1992.

Peppelenbosch et al., "Epiderman Growth Factor–Induced Actin Remodeling Is Regulated by 5–Lipoxygenase and Cyclooxygenase Products," *Cell*, 74:565–575, 1993.

Rao et al., "Hydrogen peroxide–induced c–fox expression is mediated by arachidonic acid release: role of protein kinase C," *Nucleic Acids Research*, 21(5):1259–1263, 1993.

Sherman et al., "Regulation of Tumor Necrosis Factor Gene Expression by Ionizing Radiation in Human Myeloid Leukemia Cells and Peripheral Blood Monocytes," *J. Clin. Invest.*, 87:1794–1797, 1991.

Kastan et al., "A mammalian cell cycle checkpoint pathway utilizing p53 and GADD45 is defective in ataxia–telagiectasia." *Cell*, 71:587–597, 1992.

Rosenfeld et al., "In vivo transfer of the human cystic fibroisis transmembrane conductance regulator gene to the airway epithelium." *Cell*, 68:143–155, 1992.

Ward et al., "The pulmonary response to sublethal thoracic irradiation in the rat." *Rad. Res.*, 136:15–21, 1993.

Ward et al., "The effects of steroids on radiation–induced lung disease in the rat." *Rad. Res.*, 136:22–28, 1993.

Weichselbaum et al., "Radiation induction of immediate early genes: effectors of the radiation–stress response." *Int. J. Rad. Oncol.*, 30:229–234, 1994.

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 18 amino acids
      (B) TYPE: amino acid
      (D) TOPOLOGY: linear (ii) MOLECULE TYPE: peptide (xi) SEQUENCE DESCRIPTION: SEQ ID NO:1:

```
Gln Lys Arg Pro Ser Ser Ser Ser Ser Ser Ser Gln Arg Ser Lys
  1               5                  10                  15

Tyr Leu
```

(2) INFORMATION FOR SEQ ID NO:2:

(i) SEQUENCE CHARACTERISTICS:
      (A) LENGTH: 18 amino acids
      (B) TYPE: amino acid
      (D) TOPOLOGY: linear (ii) MOLECULE TYPE: peptide -continued (xi) SEQUENCE DESCRIPTION: SEQ ID NO:2:

Arg Phe Ala Arg Lys Gly Ala Leu Arg Gln Lys Asn Val His Glu Val
 1               5                  10                  15

Lys Asn

PHOSPHOLIPASE A2 INHIBITORS AS MEDIATORS OF GENE EXPRESSION

The present application is a continuation-in-part of pending U.S. patent application Ser. No. 08/192,107, filed Feb. 4, 1994, now abandoned. The entire text of the above-referenced disclosure is specifically incorporated by reference herein without disclaimer.

The government owns rights in the present invention pursuant to NIH grant numbers CA58508, CA41068, CA55241, and CA37435.

BACKGROUND OF THE INVENTION

1. Field of the Invention

The present invention relates generally to the fields of radiation biology and cell biology. More particularly, it concerns the attenuation of the effect of ionizing radiation induced activation of tumor necrosis factor by inhibitors of extranuclear signal transduction.

2. Description of the Related Art

Signaling pathways activated by DNA damage contribute to survival of prokaryotes and eukaryotic cells following exposure to x-rays or UV light. In irradiated *E. coli*, damaged DNA forms a complex with the Rec A protease resulting in the transcriptional induction of a variety of genes including those encoding DNA repair enzymes (Walker, 1985). In yeast, UV light and x-rays result in the induction of genes which participate in the repair of damaged DNA (Jones et al., 1991, Cole et al., 1987). Genes whose products are proposed to recognize damaged or un-replicated DNA and to participate in intracellular signaling that regulates cell cycle progression and DNA repair have been identified in *S. cerevisiae* and *S. pombe* (House et al., 1992, Enoch et al., 1992). The complexity of this signaling pathway is demonstrated by the number of genes involved in sensing DNA damage and transmitting the signal (Enoch et al., 1992). DNA damage is presumed to be the initiating event in mammalian cell induction of stress response genes following x-ray or UV exposure (Herrlich et al., 1992, Kastan et al., 1992). However, the mechanisms of DNA damage recognition have not been identified in mammalian cells.

Signal transduction pathways activated by ionizing radiation include increased phosphotransferase activity of cytoplasmic protein kinases (Hallahan et al., 1991a, Hallahan et al., 1991b, Uckun et al., 1992). Moreover, inhibition of protein kinases blocks radiation-mediated gene induction and effects diverse biological endpoints such as apoptosis (Uckun et al., 1992), radiation survival (Hallahan et al., 1992)) and induction of the cytokine tumor necrosis factor (TNF) (Hallahan et al., 1991b). The calcium/phospholipid-dependent protein kinase (PKC) is activated within 15 seconds of ionizing radiation exposure and is extinguished by 90 seconds in human leukemia HL-60 cells (Hallahan et al., 1991b).

Phospholipase A2 inhibitors used in clinical radiotherapy to ameliorate acute and subacute sequelae include glucocorticoids and pentoxifylline,(Bianco et al., 1991, Phillips et al., 1975). Glucocorticoids are used to treat radiation induced proctitis, pneumonitis, conjunctivitis, external otitis, CNS syndromes and occasionally mucositis. Pentoxifylline is effective in preventing pneumonitis and mucositis following total body irradiation prior to bone marrow transplantation (Bianco et al., 1991). Taken together, these findings implicate phospholipase A2 in radiation induced TNF induction and the acute sequelae of radiotherapy.

Since phospholipase A2 hydrolyses phosphatidylcholine to arachidonic acid, the effects of the phospholipase A2 inhibitors mepacrine (Rao et al., 1993), and bromphenylbromide (BPB) (Peppelenbosch et al., 1993) were investigated. In addition, the effects of dexamethasone and pentoxifylline on radiation-induced fatty acid hydrolysis were studied, as these agents have been shown to inhibit phospholipase A2, reduce the production of cellular mediators of inflammation and tissue injury, and inhibit lipopolysaccharide-induced TNF production in monocytes (Strieter et al., 1988, Han et al., 1990). Moreover, glucocorticoids and pentoxifylline are employed clinically to prevent some acute toxicities of radiotherapy (Bianco et al., 1991, Phillips et al., 1975). The inventors determined that each agent attenuated arachidonic acid release into the medium of cells treated with X-rays or $H_2O_2$. Thus, extranuclear second messengers are in part responsible for radiation-mediated signal transduction and inhibition of this pathway may provide a means of attenuating the inflammatory-like response observed in irradiated tissues through the inhibition of TNF gene induction.

SUMMARY OF THE INVENTION

The present invention, in a general and overall sense, concerns methods of inhibiting the production of cytokines, for example tumor necrosis factor (TNF), following exposure of cells to ionizing radiation. In accordance with these methods, cells or tissues are contacted with phospholipase A2 inhibitors prior to exposure to ionizing radiation, reducing the production of cellular mediators of inflammation and tissue injury, and inhibiting the radiation-induced TNF production.

As used herein, "cytokine"refers to a class of molecules that are secreted by cells that affect the functions of other cells. More specifically, the cytokines of the present invention are secreted in response to ionizing radiation, and are produced as a result of or are otherwise involved in the arachidonic acid metabolic pathway.

Preferred inhibitors of phospholipase A2 include, but are not limited to mepacrine, bromphenylbromide (BPB), dexamethasone, or pentoxifylline. It will be recognized by-those skilled in the art that compounds with similar activity or derivatives of these inhibitors does not depart from the scope or spirit of the invention.

The present invention thus encompasses the use of any phospholipase inhibitor derivative that has a significant (i.e., consistently above background) inhibitory effect on phospholipase activity.

In certain embodiments of the invention, methods are provided for the treatment of acute radiation sequelae that mimic local inflammatory reactions, such as pneumonitis, proctitis, mucositis, dermatitis, and esophagitis. These consequences of radiotherapy may be associated with cytokine production, such as tumor necrosis factor, or with arachidonic acid metabolites. The methods described herein are designed to ameliorate these acute side effects associated with radiation therapy.

On other embodiments, the methods of the present invention are useful in inhibiting cytokine production in vitro following ionizing radiation exposure. The methods allow the production of certain polypeptides operatively linked to radiation inducible promoters unaffected by phospholipase A2 inhibitors, while reducing the effect of cytokines and arachadonate metabolic products produced following radiation exposure.

In this aspect, the present invention contemplates a pharmaceutical composition comprising an inhibitor of phospholipase A2 in a therapeutically effective amount and a physiologically acceptable carrier. The terms "contacted" and "exposed," when applied to a cell, are used herein to describe the process by which a phospholipase inhibitor is delivered to a target cell. Any method may be used to contact a cell with a phospholipase inhibitor, as long as the method results in decreased phospholipase A2 activity within the cell The phrases "pharmaceutically or pharmacologically acceptable" refer to molecular entities and compositions that do not produce an adverse, allergic or other untoward reaction when administered to a human. The appropriate doses for treating persons with radiation induced sequelae may be determined from a consideration of the condition to be treated and the properties of the composition being administered. This will be readily understood by those of skill in the art when in possession of the present disclosure.

A therapeutically effective amount of an inhibitor of phospholipase A2 that is combined with a carrier to produce a single dosage form varies depending upon the host treated and the particular mode of administration. A "therapeutically effective amount" is an amount of a phospholipase inhibitor or similar agent that, when administered to an animal, is effective to reduce or eliminate phospholipase A2 activity within the animal.

As is well known in the art, a specific dose level for any particular patient depends upon a variety of factors including the activity of the specific compound employed, the age, body weight, general health, sex, diet, time of administration, route of administration, rate of excretion, drug combination, and the severity of the particular disease undergoing therapy.

A composition of the present invention is typically administered orally or parenterally in dosage unit formulations containing standard, well known nontoxic physiologically acceptable carriers, adjuvants, and vehicles as desired. The term parenteral as used herein includes subcutaneous injections, intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Suitable doses for phospholipase A2 inhibitors would be for mepacrine (or quinacrine), 25 up to 200 mg every six hours for 5 doses prior to radiotherapy, and 200 mg once a day thereafter. As a further example, dosages of pentoxifylline range from 50 to 400 mg, given 3 times a day prior to and following radiotherapy. The skilled artisan is directed to "Remington's Pharmaceutical Sciences" 15th Edition for dosages of various inhibitors. Some variation in dosage will necessarily-occur depending on the condition of the subject being treated. The person responsible for administration will, in any event, determine the appropriate dose for the individual subject. Moreover, preparations for human administration should meet sterility, pyrogenicity, general safety and purity standards as required by the FDA Office of Biologics standards.

As used herein, the term "irradiated cell" means a cell or tissue that has been exposed to an effective expression-inducing dose of ionizing radiation that stimulates or turns on a radiation responsive enhancer-promoter or causes a physiological response in the cell, and depends on the given cell type.

As used herein, the phrase "enhancer-promoter" means a composite unit that contains both enhancer and promoter elements. As used herein, a "radiation responsive enhancer-promoter" indicates an enhancer-promoter whose transcription controlling function is affected by ionizing radiation. Typically, upon exposure to an effective dose of ionizing radiation, a radiation responsive enhancer-promoter of the present invention stimulates or increases the rate of transcription of an encoding region controlled by that enhancer-promoter. An exemplary and preferred enhancer-promoter for use in a DNA molecule of the present invention is a CArG domain of an Egr-1 promoter, a promoter for tumor necrosis factor-alpha (TNF-α) gene or a c-Jun promoter.

A radiation responsive enhancer-promoter is operatively linked to an encoding region that encodes at least one polypeptide. As used herein, the phrase "operatively linked" means that an enhancer-promoter is connected to an encoding region in such a way that the transcription of that encoding region is controlled and regulated by that enhancer-promoter. Means for operatively linking an enhancer-promoter to an encoding region are well known in the art. As is also well known in the art, the precise orientation and location relative to an encoding region whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

In one embodiment, an encoding region of a DNA molecule of the present invention encodes a single polypeptide. As used herein, the term "polypeptide" means a polymer of amino acids connected by amide linkages, wherein the number of amino acid residues can range from about 5 to about one million. Preferably, a polypeptide has from about 10 to about 1000 amino acid residues and, even more preferably from about 20 to about 500 amino residues. Thus, as used herein, a polypeptide includes what is often referred to in the art as an oligopeptide (5–10 amino acid residues), a polypeptide (11–100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Any polypeptide can be encoded by an encoding region of a DNA molecule of the present invention. An encoding region can comprise introns and exons so long as the encoding region comprises at least one open reading frame for transcription, translation and expression of that polypeptide. Thus, an encoding region can comprise a gene, a split gene or a cDNA molecule. In the event that the encoding region comprises a split gene (contains one or more introns), a cell transformed or transfected with a DNA molecule containing that split gene must have means for removing those introns and splicing together the exons in the RNA transcript from that DNA molecule if expression of that gene product is desired.

In a preferred embodiment an effective expression inducing amount is from about 2 to about 20 Gray (Gy) administered at a rate of from about 0.5 to about 2 Gy/minute. Even more preferably, an effective expression inducing amount of ionizing radiation is from about 5 to about 15 Gy.

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

Cells containing a DNA molecule of the present invention encoding a particular polypeptide express that polypeptide when exposed to ionizing radiation.

DETAILED DESCRIPTION OF THE PREFERRED EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I
Inhibition of Phospholipase A2 and Ionizing Radiation Gene Expression
Arachidonic Acid Assay HL-60 cells in logarithmic growth were incubated for 16 h in RPMI 640 medium supplemented with 1.0 mg/ml fatty acid free bovine serum albumin and 0.2 $\mu$Ci/ml [$^3$H] arachidonic acid as described (Spriggs et al., 1990, Godfrey et al., 1987). Mepacrine 20 $\mu$M, BPB 10 $\mu$M, dexamethasone 1 $\mu$M, or pentoxifylline (3,7-dimethyl-1-(5-oxo-hexyl)-xanthine, Hoffman-La Roche, Basel, Switzerland) 1 mM were added to labeled cells 1 hr prior to irradiation with 10 Gy at 1 Gy/min. At the indicated times, a 1 ml aliquot of supernatant was assayed by the addition of Hydrofluor™ and scintillation counting.

Diacylglycerol (DAG) Kinase Assay

DAG release from irradiated cells was quantified as previously described (Wright et al., 1988). Serum deprived HL-60 cells were pelleted and irradiated (10 Gy at 2.5 Gy/sec) and 100% methanol was added immediately on ice. Extracts were dried under $N_2$ and resuspended into cardiolipin and n-octylglucoside and bacterial DAG kinase in the presence of $^{32}$P-ATP. Cellular DAG was quantified by using a known concentration of synthetic DAG reacted with DAG kinase. Bradykinin was used as a positive control and resulted in a 3.0±0.4 fold increase in DAG, while x-irradiation produced DAG levels 1.2±0.4 as compared to untreated controls.

Assay of Protein Kinase C (PKC) Activity

AT cells were grown to confluence and serum deprived for 24 hours. Medium was aspirated, cells were washed with PBS and then γ-irradiated with 10.8 Gy using a Cobalt-60 source (Gammacell 220) at a dose rate of 2.7 Gy/second. Protein was extracted on ice at 15 second intervals following irradiation by the addition of 0.4 ml of lysis buffer (20 $\mu$M Tris/HCl, pH 7.5, 0.5 mM EDTA, 0.5 mM EGTA, and 2-mercaptoethanol 10 mM (TEM) with 0.5% Triton X100, and 25 $\mu$g/ml each leupeptin and aprotinin). Cells were homogenized and protein was partially purified as previously described (Hallahan et al., 1990b). Protein extract (25 $\mu$l) was added to 25 $\mu$l of TEM, 5 $\mu$l of phospholipid (2.8 mg/ml phosphatidyl serine and 10 mM phorbol ester in Triton X100 mixed micelles, GIBCO) (Yasuda et al., 1990) and 10 $\mu$l of $^{32}$P-ATP/substrate containing 5×10$^7$ CPM/ml of $^{32}$P-ATP (New England Nuclear), 100 $\mu$M ATP, 250 $\mu$M synthetic peptide Gln-Lys-Arg-Pro-Ser(8)-Gln-Arg-Ser-Lys-Tyr-Leu (SEQ ID NO:1), 5 mM CaCl, 100 mM MgCl$_2$ (GIBCO) (Yasuda et al., 1990) in 20 mM Tris HCl, pH 7.5. Following incubation for 5 min at 30° C., samples were dried on phosphocellulose and washed in 1% H$_3$PO$_4$ twice for 5 minutes followed by washing in H$_2$O twice for 5 min. Scintillation counts of each sample and 10 $\mu$l of unwashed $^{32}$P-ATP/substrate were performed. To calculate the rate of $^{32}$P incorporation into the peptide substrate, 100 $\mu$M of synthetic PKC specific inhibitor peptide (Arg-Phe-Ala-Arg-Lys-Gly-Ala Leu-Arg-Gln-Lys-Asn-Val-His-Glu-Val-Lys-Asn(SEQ ID NO:2)) (GIBCO) (House et al., 1989) in 20 mM Tris 7.5 was added to PKC assays prior to 32P-ATP/substrate and samples were incubated, washed and counted as described above. Background $^{32}$P incorporation was subtracted from that of assays without inhibitor and the rate of $^{32}$P incorporated into the peptide substrate was calculated (pmol/min) as previously described (Hallahan et al., 1990 b, Yasuda et al., 1990). Phosphorylation rates were normalized to 10$^6$ cells per assay.

To determine the effects of PLA2 inhibitors on radiation-mediated PKC activation, mepacrine, BPB, dexamethasone or pentoxifylline were added to HL-60 cell cultures 1 hr prior to γ-irradiated with 10.8 Gy using a Cobalt-60 source (Gammacell 220) at a dose rate of 2.7 Gy/second. Cells were placed on ice and lysis buffer was added at 60 seconds following irradiation (Hallahan et al., 1991b). Phosphotransferase activity was assayed as previously described above. Phosphorylation rates were normalized to 10$^6$ cells per assay.

RNA Analysis

Cells were grown to a density of 10$^6$/ml and exposed to 10 Gy (GE Maxitron™ X-ray generator) as previously described (Hallahan et al., 1989). RNA was extracted using the single step guanidinium thiocyanate-phenol/chloroform method (Chomczynski et al., 1987) at 1 hour following irradiation. Control RNA from nonirradiated cells treated with otherwise identical conditions and RNA from irradiated cells was size fractionated by 1% agarose formaldehyde electrophoresis. Ethidium bromide staining of the RNA demonstrated equal loading of each lane. RNA gels were then transferred to a nylon membrane (Genescreen Plus™, New England Nuclear). Northern blots were hybridized to the $^{32}$P labeled TNF cDNA probe (Spriggs et al., 1990) followed by autoradiography for 3 days at −85° C. with intensifying screens. 7S RNA hybridization was used to demonstrate equal loading of lanes. Mepacrine, dexamethasone, BPB, or pentoxifylline were added to HL-60 cell cultures 1 hr prior to irradiation with 10 Gy (1 Gy/min) using a GE Maxitron generator.

Results

1. The Effects of the Phospholipase A2 Inhibitors on Radiation-induced Fatty Acid Hydrolysis Arachidonic acid production was quantified in irradiated HL-60 cells which have served as a model for the study of radiation-mediated TNF gene induction and PKC-dependent signal transduction (Hallahan et al., 1991b). HL-60 cells were incubated with [$^3$H]arachidonic acid for 3 hours, washed, irradiated with 10 Gy at 1 Gy/min.

The HL-60 cells in logarithmic growth were incubated for 16 hours in RPMI 640 medium supplemented with 1.0 mg/ml fatty acid free bovine serum albumin and 0.2 μCi/ml [$^3$H] arachidonic acid as described (Spriggs et al., 1990, Godfrey et al., 1987). Mepacrine 20 uM, BPB 10 gM, Dexamethasone 1 μM, or pentoxifylline (3,7-dimethyl-1-(5-oxo-hexyl)-xanthine, Hoffman-La Roche, Basel, Switzerland) 1 mM were added to labeled cells 1 hr prior to irradiation with 10 Gy at 1 Gy/min. At the indicated times, a 1 ml aliquot of supernatant was assayed by the addition of Hydrofluor and scintillation counting.

Fatty acid release into the medium was significantly increased following irradiation. Previous work has also shown that arachidonic acid release is increased following treatment with $H_2O_2$ (Gustafson et al., 1991, Shasby et al., 1988), which served as a positive control. To confirm that arachidonate was produced, the inventors performed gas chromatographic analysis of lipids extracted from irradiated HL-60 cells. Using this approach, an increase in arachidonate was detectable at 30 minutes following irradiation. Conversely, Diacylglycerol levels did not change following irradiation as determined by the DAG kinase assay.

The effects of the phospholipase A2 inhibitors mepacrine, bromphenylbromide (BPB) dexamethasone, and pentoxifylline on radiation-induced fatty acid hydrolysis were studied. Each attenuated arachidonic acid release into the medium of cells treated with X-rays or $H_2O_2$. Since PKC has been shown to activate phospholipase-mediated hydrolysis of membrane phospholipids (Godson et al., 1990, Sporn et al., 1990), the PKC inhibitor H7 was added to determine whether PKC activation contributes to lipid hydrolysis following irradiation. H7 pretreatment had no detectable effect on arachidonic acid release following irradiation of HL-60 cells. This is consistent with the finding that PKC inhibition produced no reduction in arachidonic acid release following $H_2O_2$ treatment (Sporn et al., 1990).

2. The Effects of the Phospholipase A2 Inhibitors on Radiation-induced Protein Kinase C Activation PKC phosphotransferase activity is increased following the addition of arachidonate (Peters-Golden et al., 1991, McPhail et al., 1984). Taken together with the findings that PKC is activated rapidly and transiently following ionizing radiation exposure and that PKC activity is required for radiation-induced TNF gene induction in HL-60 cells (Hallahan et al., 1991b), these data suggested that arachidonate activation of PKC might be the signalling pathway which confers TNF induction. To determine whether radiation-induced arachidonate production is associated with PKC activation, the phosphotransferase activity of PKC was quantified in irradiated HL-60 cells pretreated with phospholipase A2 inhibitors.

Mepacrine μM, BPB, Dexamethasone or pentoxifylline were added to HL-60 cell cultures 1 hr prior to γ-irradiated with 10.8 Gy using a Cobalt-60 source (Gammacell 220) at a dose rate of 2.7 Gy/second. Cells were placed on ice and lysis buffer was added at 60 seconds following irradiation as described (9). Phosphotransferase activity was assayed as previously described (Hallahan et al. 1991b) using $^{32}$P-ATP/ substrate containing 5×10$^7$ CPM/ml of $^{32}$P-ATP (New England Nuclear) and synthetic peptide Gln-Lys-Arg-Pro-Ser(8)-Gln-Arg-Ser-Lys-Tyr-Leu(SEQ ID NO:1). Phosphorylation rates were normalized to 10$^6$ cells per assay.

Protein was extracted at 60 seconds following irradiation, and phosphotransferase activity was quantified in vitro. The PKC specific peptide substrate from myelin basic protein (Yasuda et al., 1990) and the PKC inhibitor peptide from the PKC regulatory domain (House et al., 1987) were employed to quantify PKC activity following irradiation. A 3-fold increase in phosphotransferase activity was found at 45 seconds following irradiation as compared to untreated control cells. Mepacrine, BPB, pentoxifylline and dexamethasone, added 1 hr prior to irradiation, reduced the X-ray induced increase in PKC phosphotransferase activity. These data are in concordance with a previously undescribed x-ray-induced signalling pathway following x-ray exposure, whereby oxidized membrane phospholipids are hydrolyzed to arachidonate which in turn activates PKC.

3. The Effects of the Phospholipase A2 Inhibitors on Radiation-induced TNF Gene Expression Although transcription of certain radiation-inducible genes occurs through both PKC-dependent and independent signalling pathways (Datta et al., 1992), TNF induction is dependent upon PKC activation (Hallahan et al., 1991b) and thus represents a radiation-mediated gene which can be studied to determine the significance of phospholipase inhibition on radiation-mediated gene induction.

Mepacrine 20 μM, Dexamethasone, BPB, or pentoxifylline were added to HL-60 cell cultures 1 hr prior to irradiation with 10 Gy (1 Gy/min) using a GE Maxitron generator. RNA was extracted at 1 hour after irradiation as previously described (Hallahan et al., 1989). Control RNA from non-irradiated cells treated under otherwise identical conditions and RNA from irradiated cells was size fractionated by 1% agarose formaldehyde electrophoresis and hybridized to a $^{32}$P labeled TNF cDNA probe (Sherman et al., 1991). 7S RNA hybridization was used to demonstrate equal loading of lanes. RNA was isolated 1 hr following irradiation at the time of peak TNF expression.

The finding that each of these agents each blocked radiation-induced TNF gene expression indicated that radiation-induced TNF expression is dependent on signaling through phospholipase-A2. Moreover, attenuation of radiation-mediated gene induction by these phospholipase A2 inhibitors suggests that signal transduction activated by ionizing radiation is in part initiated through hydrolysis of oxidized membrane lipids.

Discussion

Second messengers such as diacylglycerol (DAG), arachidonic acid and calcium participate in PKC activation in response to a number of external stimuli (Nishizuka 1992). The inventors have investigated the mechanism of PKC activation following irradiation by analyzing the second messengers diacylglycerol, arachidonic acid and calcium which participate in PKC activation in response to a number of external stimuli (Nishizuka 1992). It was found that diacylglycerol levels were not increased following irradiation as determined by the DAG kinase assay. Furthermore, intracellular calcium flux did not occur as determined by quantifying UV absorption in fura-2 treated cells during irradiation with $^{90}$Sr (60 cGy/sec) (Hallahan et al., 1994). Taken together, these data support the finding that phosphoinositol-specific phospholipase C is not activated during irradiation since the coincident increase in inositol triphosphate would mobilize intracellular Ca$^{++}$.

The acute effects of ionizing radiation on the lung has been shown to be associated with endothelial leakage (Ward et al., 1993a). Corticosteroids prevent the acute effect when given to animals at the tie of irradiation, but this treatment did not affect lung fibrosis (Ward et al., 1993b) indicating that steroids prevent the inflammatory component of radiation injury but not the fibrotic component. In the present study, arachidonic acid release was reduced when irradiated cells were pretreated with pentoxifylline, dexamethasone or BPB. These findings are significant in that the reduction in radiation-mediated phospholipase A2 activity in turn diminished PKC activation and TNF induction.

Lipid oxidation occurs in the cell membrane of irradiated cells (Yatvin et al., 1979). Indeed, the probable mechanism of arachidonic acid release following irradiation is phospholipase $A_2$-mediated hydrolysis of oxidized membrane lipids. In support of this hypothesis, whole body irradiation of animal models results in increased arachidonic acid metabolites (Eldor et al., 1979). Oxidative injury following $H_2O_2$ treatment results in phospholipase $A_2$-mediated arachidonic acid release in epithelial and endothelial cells (Gustafson et al., 1991, Au et al., 1987, Sevanian et al., 1983).

Phosphatidylcholine hydrolysis to arachidonic acid is reduced by pentoxifylline in platelets stimulated with thrombin (Rossignol et al., 1988). In concert with these findings and the demonstration that arachidonic acid activates PKC both in vitro (34,35,36) and in vivo (Sporn et al., 1990, Khan et al., 1991, Fan et al., 1990, Lester et al., 1991) the inventors have found that inhibition of phospholipase A2 attenuates radiation-induced PKC activation. These results demonstrate for the first time that fatty acid hydrolysis an early step in a signalling pathway activated by ionizing radiation which may be independent of DNA damage. On the basis of these results, it is surmised that evolution of phospholipase A2-dependent signaling pathways provides a mechanism for higher eukaryotes to respond to reactive oxygen intermediates with cytokine production. In support of this consideration, Neta et al have shown that TNF protects hematopoietic cells from killing by ionizing radiation (Neta et al., 1991).

A practical application of these findings relates to reduction of radiation sequelae during the treatment of cancer. Although the effects of ionizing radiation on proliferating cell renewal systems are theorized to be due to the direct killing effects of radiation on stem cells within the injured organ, other work has suggested that TNF induction plays a role in the acute effects of radiation therapy (reviewed in Weichselbaum et al., 1993). For example, elevated TNF serum levels in patients receiving total body irradiation prior to bone marrow transplantation is associated with a greater incidence of complications such as mucositis, pneumonitis, hepatitis and nephritis than in patients with relatively lower TNF serum levels (Holler et al., 1992). Because TNF induction is associated with acute and subacute complications of therapeutic radiation, inhibition of phospholipase A2 represents a novel means of abating these sequelae. Indeed, pharmacologic agents used to ameliorate the acute and subacute sequelae of radiotherapy include glucocorticoids and pentoxifylline (Phillips et al., 1975, Gross, 1980, Bianco et al., 1991). For example, acute effects of radiation, such as pneumonitis and the central nervous system syndrome, have been abated by these drugs (Phillips et al., 1975).

The identification of a signal transduction pathway responsible for radiation-mediated arachidonic acid production, PKC activation and TNF induction may allow for rational design of radioprotective drugs that do not adversely affect tumor cure rates and avoid the serious side effects of glucocorticoids. Such strategies of radioprotection offer new avenues to enhance the therapeutic ratio in clinical oncology.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Au, A., Chan, P., & Fishman, R. (1985) *J. Cell. Biochem.* 27, 449–53.

Bell, R. M., Hannun, Y. & Loomis, C. (1986) *Meth Enzym* 124, 353–7.

Bianco, J., Applebaum, F., Nemunaitis, J., Almgren, J., Andrews, F., Kettner, P., Shields, A. and Singer, J. W. (1991) *Blood* 78, 1205–11.

Chomczynski, P. & Sacchi, N. (1987) *Analytical Biochemistry* 162, 156–9.

Cole, G., Schild, D., Lovett, S. & Mortimer, R. (1987) *Molec Cell Biol* 7, 1078–84.

Datta, R., Hallahan, D., Kharbanda, S., Rubin, E., Sherman, M., Huberman, E., Weichselbaum, R. & Kufe, D. (1992) *Biochemistry* 31, 8300–6.

Eldor, A., Vlodavsky, I., Fuks, Z., Matzner, Y. & Rubin, D. B. (1989) *Prostaglandins leukotrienes and essential fatty acids* 36, 251–8.

Enoch, T., Carr, A. & Nurse, P. (1992) *Genes Devel.* 6, 2035–46.

Fan, X. T., Huang, X. P., Da, S. C. & Castagna, M. (1990) *Biochem Biophys Res Commun* 169, 933–40.

Godfrey, R., Johnson, W. & Hoffstein, S. (1987) *Biochem Biophys Res Commun* 142, 235–41.

Godson, C., Weiss, B. A. & Insel, P. A. (1990) *J Biol Chem* 265, 8369–72.

Gross, N. J. (1980) *J Clin Invest* 66, 504–10.

Gustafson, C., Lindahl, M. & Tagesson, C. (1991) *Scand. J. Gastroenterol* 26, 237–47.

Hallahan, D., Virudchalam, S., Schwartz, J., Panje, N., Mustafi, R. & Weichselbaum, R. (1992) *Radiat. Res.* 129, 345–50.

Hallahan, D. E., Sukhatme, V. P., Sherman, M. L., Virudachalam, S., Kufe, D. W. & Weichselbaum, R. R,. (1991) *Proc. Natl. Acad. Sci.* 88, 2152–60.

Hallahan, D., Virudachalam, S., Sherman, M., Kufe, D. & Weichselbaum, R. (1991) *Cancer Research* 51, 4565–9.

Hallahan, D. E., Spriggs, D. R., Beckett, M. A., Kufe, D. W. & Weichselbaum, R. R. (1989) *Proc Natl Acad Sci USA* 86, 10104–7.

Hallahan, D. E., Bleakman, D., Virudachalam, S., Lee, D., Grdina, D., Kufe, D. & Weichselbaum, R. (1994) *Rad Res.* In Press.

Han, J., Thompson, P. & Beutler, B. (1990) *J. Exp. Med.* 172, 391–6.

Herrlich, P., Ponta, H. & Rahmsdorf, H. (1992) *Rev. Physiol. Biochem. Pharmacol.* 119, 187–223.

Holler, E., Kolb, H., Moller, A., Kempeni, J., Liesenfeld, S., Pechumer, H., Lehmacher, W., Ruckdeschel, G., Gleixner, B., Riedner, C., Ledderose, G., Brehm, G., Mittermuller, J. and Wilmanns, W. (1990) *Blood* 75, 1011–16.

House, C. & Kemp, B. E. (1987) *Science* 238, 1726–28.

Jones, J. & Prakash, L. (1991) *Nucl. Acid Res.* 19, 893–5.

Khan, W., el, T. S. & Hannun, Y. A. (1991) *Febs Lett* 292, 98–102.

Kastan, M., Zhan, Q., El-Deiry, W., Carier, F., Jacks, T., Walsh, W., Plunkett, B., Vogelstein, B. & Fornace, A. (1992) *Cell* 71, 587–97.

Lester, D. S., Collin, C., Etcheberrigaray, R. & Alkon, D. L. (1991) *Biochem Biophys Res Commun* 179, 1522–6.

Lognonne, J. L., Ducousso, R., Rocquet, G. & Kergonou, J. F. (1985) *Biochime* 67, 1015–21 44. G. Hahn, M. Menconi, M. Cahill & P. Polgar. (1983) *Prostaglandins* 25, 783–91.

McPhail, L., Clayton, C. & Snyderman, R. (1984) *Science* 224, 622–5.

Murakami, K., Chan, S. & Routtenberg, A. (1986) *J. Biol. Chem.* 261, 15424–9.

Neta, R., Oppenheim, J. J., Schreiber, R. D., Chizzonite, R., Ledney, G. D. & MacVittie, T. J. (1991) *J. Exp. Med.* 173, 1177–82.

Nishizuka, Y. (1992) *Science* 258, 607–14.

Peppelenbosch, M., Tretoolen, L., Hage, W. & de Laat, S. (1993) *Cell* 74, 565–15.

Peters-Golden, M., McNish, R. W., Sporn, P. H. & Balazovich, K. (1991) *Am J Physiol.* 261, L462–71.

Phillips, T., Wharam, M. & Margolis, L. (1975) *Cancer* 35, 1678–84.

Rao, G., Lassegue, B., Griendling, K., Alexander, R. & Berk, B. (1993) *Nucl. Acid. Res.* 21, 1259–63.

Rossignol, L., Plantavid, M., Chap, H. & Douste-Blazy, L. (1988) *Biochem Pharm* 37, 3229–36.

Sambrook et al. (1989). Molecular cloning: A laboratory manual. Cold Spring Harbor Laboratory. Cold Spring Harbor, N.Y. Sevanian, A., Kelly,. S. & Montestrugue, S. (1983) *Arch. Biochem Biophys.* 223, 441–52.

Shasby, D., Winter, M. & Shasby, S. (1988) *Cell Physiol* 24, C781–8.

Sherman, M. L., Datta, R., Hallahan, D., Weichselbaum, R. R. & Kufe, W. (1991) *J. Clin. Invest.* 87, 1794–7.

Sporn, P. H., Marshall, T. M. & Peters-Golden, M. (1990) *Biochim Biophys Acta* 1047, 187–91.

Spriggs, D., Sherman, M., Imamura, K., Mohri, M., Rodriguez, C., Robbins, G. & Kufe, D. (1990) *Cancer Res.* 50, 7101–7.

Strieter, R. M., Remick, D. G., Ward, P. A., Spengler, R. N., Lynch, J. P. III, Larrick, J. & Kunkel, S. L. (1988) *Biochem. Biophys. Res. Comm.* 155, 1230–6.

Uckun, F., Tuel-Ahlgren, L., Song, C., Waddick, K., Myers, D., Kirihara, J., Ledbetter, J. & Schieven, G. (1992) *Proc. Natl Acad Sci* 89, 9005–9.

van Kuijk, F. J., Handelman, G. J. & Dratz, E. A. (1987) *Trends Biochem Sci* 12, 31–4.

Walker, G. C. (1985) *Ann. Rev. Biochem.* 54, 425–57.

Ward, H., Kemsley, L., Davies, L., Holecek, M. & Berend, N. (1993) *Rad. Res.* 136, 15–21.

Ward, H., Kemsley, L., Davies, L., Holecek, M. & Berend, N. (1993) *Rad. Res.* 136, 2–8.

Weichselbaum, R., Hallahan, D. & Chen, G. in *Biological and physical basis to radiation oncology*, eds. Holland & Frei (Lea and Febiger, Malvern, P A; 1993). Wright, T., Rangan, L., Shin, H., Raben, D. (1988) *J. Biol. Chem.* 263, 9374–80.

Yasuda, I., Kishimoto, A., Tanaka, S.-I., Masahiro, T., Sakurai, A. & Nishizuka, Y. (1990) *Biochem. and Biophys Res Comm.* 166, 1220–7.

Yatvin, M., Gipp, J. & Dennis, W. (1979) *Int. J. Rad. Biol.* 25, 539–48.

Zhou, Z. & Elledge, S. (1992) *Genetics* 131, 851–66.

---

What is claimed is:

1. A method of inhibiting tumor necrosis factor production in a cell exposed to ionizing radiation comprising contacting the cell with an amount of a phospholipase A2 inhibitor, prior to said irradiation, effective to inhibit tumor necrosis factor production in said cell.

2. The method of claim 1, wherein the phospholipase A2 inhibitor is mepacrine, bromphenylbromide (BPB), dexamethasone, or pentoxifylline.

3. A method of inhibiting tumor necrosis factor production in a patient in need of ionizing radiotherapy comprising administering to the patient a dose of a phospholipase A2 inhibitor, prior to said ionizing radiotherapy, effective to inhibit tumor necrosis factor production in said patient.

4. The process of claim 3, wherein the patient has cancer.

5. The process of claim 3, wherein the phospholipase A2 inhibitor is mepacrine, bromphenylbromide (BPB), dexamethasone, or pentoxifylline.

6. A method of reducing acute ionizing radiation a sequelae in a patient comprising administering to the patient, prior to said radiation dose of a phospholipase A2 inhibitor effective to reduce said sequelae in said patient.

7. The process of claim 6, wherein the radiation sequelae are mucositis, pneumonitis, nephritis, proctitis, conjunctivitis, and external otitis.

8. The process of claim 6, wherein the phospholipase A2 inhibitor is mepacrine, bromphenylbromide (BPB), dexamethasone, or pentoxifylline.

* * * * *

UNITED STATES PATENT AND TRADEMARK OFFICE
CERTIFICATE OF CORRECTION

PATENT NO. : 6,486,170 B1
DATED : November 26, 2002
INVENTOR(S) : Hallahan et al.

It is certified that error appears in the above-identified patent and that said Letters Patent is hereby corrected as shown below:

Column 14,
Line 14, please delete "a" after "radiation" therefor
Line 16, please insert -- a -- before "dose" therefor Signed and Sealed this Fourth Day of March, 2003

JAMES E. ROGAN
*Director of the United States Patent and Trademark Office*